United States Patent
Tatsumi et al.

(10) Patent No.: US 7,214,506 B2
(45) Date of Patent: May 8, 2007

(54) METHOD FOR TREATING ONYCHOMYCOSIS

(75) Inventors: Yoshiyuki Tatsumi, Otsu (JP); Mamoru Yokoo, Otsu (JP); Kosho Nakamura, Moriyama (JP); Tadashi Arika, Suita (JP)

(73) Assignee: Kaken Pharmaceutical Co., Ltd., Bunkyo-ku, Tokyo (JP)

( * ) Notice: Subject to any disclaimer, the term of this patent is extended or adjusted under 35 U.S.C. 154(b) by 451 days.

(21) Appl. No.: 10/685,266

(22) Filed: Oct. 14, 2003

(65) Prior Publication Data

US 2007/0082375 A1    Apr. 12, 2007

Related U.S. Application Data

(62) Division of application No. 10/031,929, filed as application No. PCT/JP00/04617 on Jul. 11, 2000, now abandoned.

(30) Foreign Application Priority Data

Jul. 28, 1999    (JP) .................................. 11/214369

(51) Int. Cl.
*C12Q 1/18*    (2006.01)
*A01N 43/26*    (2006.01)
*A01N 43/34*    (2006.01)
*A61K 31/445*    (2006.01)

(52) U.S. Cl. ....................................... 435/32; 514/326
(58) Field of Classification Search ............... 435/32; 514/326
See application file for complete search history.

(56) References Cited

U.S. PATENT DOCUMENTS

| | | | | |
|---|---|---|---|---|
| 5,620,994 A | * | 4/1997 | Naito et al. | ................. 514/326 |
| 5,716,969 A | * | 2/1998 | Naito et al. | ................. 514/326 |
| 5,962,476 A | | 10/1999 | Naito et al. | |

FOREIGN PATENT DOCUMENTS

| | | |
|---|---|---|
| EP | 0 402 989 A2 | 12/1990 |
| JP | 8-103291 | 4/1996 |
| JP | 10-28597 | 2/1998 |
| WO | WO 94/26734 | 11/1994 |
| WO | WO 99/39680 A1 | 8/1999 |

OTHER PUBLICATIONS

Kitazaki Tomoyuki et al., Chem. Pharm. Bull, vol. 44 (No. 2), p. 314-327, (Feb. 1996).
Ogura, Hironobu et al., Chem. Pharm. Bull, vol. 47 (No. 10), p. 1417-1425, (Oct. 1999).

* cited by examiner

*Primary Examiner*—Jon Weber
*Assistant Examiner*—Kailash C. Srivastava
(74) *Attorney, Agent, or Firm*—Nixon Peabody LLP

(57) ABSTRACT

A novel method for evaluating an effect of an antimicrobial agent which comprises removing the antimicrobial agent remaining in a biological sample or the like to thereby accurately evaluate the effect of the antimicrobial agent without being affected by the remaining antimicrobial agent. A therapeutic agent for onychomycosis which can be obtained according to the evaluation method of the drug effect.

2 Claims, 4 Drawing Sheets

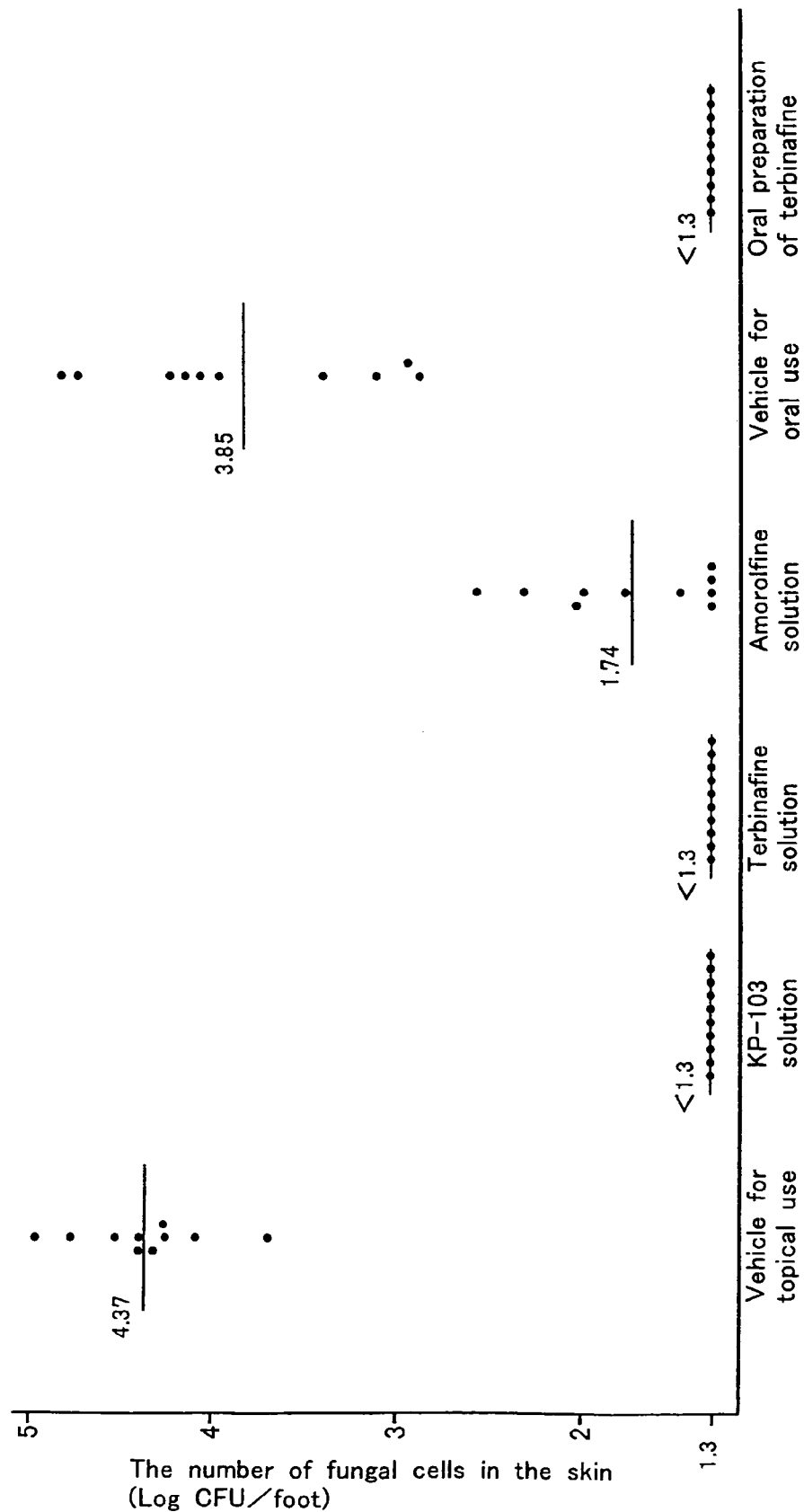

METHOD FOR TREATING ONYCHOMYCOSIS

This application is a divisional under 35 U.S.C. § 120 of U.S. Non-Provisional application Ser. No. 10/031,929 filed 25 Jan. 2002, now abandoned, which was a National Stage filing under 35 U.S.C. § 371 of PCT/JP00/04617 filed 11 Jul. 2000, which claimed priority to Japanese patent application Ser. No. 11/214,369 filed 28 Jul. 1999.

TECHNICAL FIELD

The present invention relates to a method for detecting pathogenic microorganism, method for evaluating an effect of an antimicrobial agent on pathogenic microorganism and a method for detecting an antimicrobial agent. The present invention also relates to an antimicrobial agent and a therapeutic agent for onychomycosis, which are obtained according to the above-mentioned method for evaluating the drug effect.

BACKGROUND ART

A method for evaluating a drug effect with an animal model is needed in order to explore a novel antimicrobial agent (also hereinafter referred to "drug"). Further, a method enabling a drug effect to be evaluated with accuracy is needed because of grate importance in view of predicting a clinical therapeutic efficiency thereof.

Historically, an experimental dermatophytosis model that back, planta and interdigital of a guniea pig have been infected with *Trichophyton mentagrophytes* has been used in order to evaluate an effect of an antifungal agent on dermatophytosis. Such animal models have been already employed to develop some antifungal agent. The evaluation of the effect of such antifungal agent carried out by applying the antifungal agent to the infected animal, by excising the skin after the certain period of time to cut into plural small pieces, by cultivating the skin pieces on the medium, and by counting the number of pieces wherein no growth of fungus is seen or the number of animals or feet wherein no growth of fungus is seen in all skin pieces, as an indicator (Antimicrobial Agents and Chemotherapy, 36: 2523–2525, 1992, 39: 2353–2355, 1995). Hereinafter, the conventional method for evaluating the drug effect is referred to as "the conventional method".

Although the drug having a potent activity against *Trichophyton* in vitro such as lanoconazole or amorolfine has been marketed in these days, an improvement of cure rate in a clinical use is hardly seen. As a main reason thereof, a relapse that since fungus in the skin is not completely killed after a treatment, the fungus grow again is pointed.

In also animal experiments, when an effect of lanoconazole on guniea pig models of tinea pedis was evaluated using the conventional method, though "fungus-negative" was observed in all feet out of 20 feet 2 days after the last treatment, a relapse was observed in 11 out of 20 feet 30 days after the last treatment, and no correlation was seen between the effect 2 days after the last treatment and the effect 30 days after the last treatment (36th Interscience Conference on Antimicrobial Agents and Chemotherapy, New Orleans, La., 1996, Abstr. F80).

As a reason thereof, there were followings. Since lanoconazole have very potent antitrichophyton activity in vitro, lanoconazole persisted in the skin 2 days after the last treatment in the concentration wherein the sterilization effect was shown. Therefore, when the skin is excised and cultivated on the medium to detect fungus, the lanoconazole remaining in the skin is diffused in the medium, and therefore, no fungus was detected due to prevention of the growth regardless of the presence of viable fungus in the excised skin. On the other hand, since the concentration of the drug remained in the skin is reduced 30 days after the last treatment, fungus in the skin can grow again and can be detected by culture study.

According to this hypothesis, it is ascertained that the drug remain in the skin through the inhibition of the growth of fungus around the skin blocks completely, when the lanoconazole-treated skin blocks were located and cultivated on the medium which contains dermatophytes.

Therefore, it became to clear that the conventional method has the problem that the drug effect can not be accurately evaluated, because the apparent therapeutic effect need to be evaluated after removing the drug remaining in the skin.

Meanwhile, a kind of mycosis, dermatophytosis, is the superficial dermatosis which is caused by dermatophyte parasitizing the keratin such as skin (stratum corneum), the nail and the hair. In particular, tinea unguium formed in the nail is known as the intractable disease among dermatomycoses based on dermatophytoses, and is accompanied by symptom such as opacity, tylosis, destruction and deformation of nail plate. Now the oral preparation (such as griseofulvin or terbinafine) is used for the treatment of such tinea unguium. However, there are many cases where the patient stops taking the drug or that takes the drug irregularly, since they have to take the drug for a long period, for example at least a half a year in order to completely cure tinea unguium. It is thought that this is a main cause of difficulty of curing tinea unguium completely. Furthermore, by taking the drug for a long period, griseofulvin has the problem of side effects on internal organ (gastrointestinal disorder, hepatotoxicity) and hepatotoxicity is reported as the side effect in terbinafine. Therefore, in order to improve the compliance of the patient it is desired to develop a topical preparation which cure tinea unguium for a short period and has less the systemic side effect than the oral preparation.

However, in case of the simple application on nail plate with the current antifungal agent for topical use, the antifungal effect on fungus in the nail was not seen, because the drug could not sufficiently permeate the thick keratin in nail plate (Markus Niewerth and Hans C. Korting, Management of Onychomycoses, Drugs, 58: 283–296, 1999).

In addition, the therapeutic effect of a topical preparation of antifungal agent on the experiment model of trichophytosis can not be evaluated using the conventional method as mentioned above. This may be a reason why the drug effect on the guniea pig model of tinea unguium has been hardly reported.

DISCLOSURE OF INVENTION

The present invention has been accomplished based on findings that it is desirable that an effect of antimicrobial agent such as particularly antifungal agent is evaluated after removing a drug remaining in the infected site after treatment of an animal or a biosample such as skin with the pathogenic microorganism. An object of the present invention is to provide a novel method for evaluating the effect of the antimicrobial agent and the antimicrobial agent obtained according to the method for evaluating the drug effect. In detail, the present invention provides the method for detecting the viable pathogenic microorganism in the abovementioned infected site of the animal or the biosample with the pathogenic microorganism after removing the antimicrobial agent which has been administered to the animal or the biosample, and the method for evaluating the effect of antimicrobial agent which can accurately evaluate the effect of the antimicrobial agent without the influence of the antimicrobial agent remaining in the infected site of the animal or the biosample with a pathogenic microorganism. In addition, the present invention provides the antimicrobial agent obtained according to the above-mentioned the method for evaluating the drug effect, and the detecting method of the antimicrobial agent which comprises detecting the existing antimicrobial agent in the infected site of the animal or the biosample with the pathogenic microorganism, to which the antimicrobial agent is administered.

In more detail, according to the present invention a detection of a pathogenic microorganism and an evaluation of an effect of an antimicrobial agent can be carried out by infecting an animal or a biosample with the pathogenic microorganism, administering the antimicrobial agent comprising a compound having an antimicrobial effect or a composition thereof before or after the infection, then removing the antimicrobial agent, and thereafter detecting the viable pathogenic microorganism in the infected site with the pathogenic microorganism.

According to the present invention a detection of an existing antimicrobial agent can be carried out by infecting an animal or a biosample with a pathogenic microorganism, administering the antimicrobial agent comprising a compound having an antimicrobial effect or a composition thereof before or after the infection, then excising the infected site with the pathogenic microorganism, placing and cultivating it on a medium containing the pathogenic microorganism, and thereafter observing a growth inhibition of the pathogenic microorganism around the infected site with the pathogenic microorganism.

Additionally, an object of the present invention is to provide the evaluation method of a drug which enables the effect of an antifungal agent to accurately evaluate in a guinea pig model of tinea unguium. Another object of present invention is to provide a therapeutic agent for onychomycosis which exhibits the effect on tinea unguium by topical application and which is capable of curing tinea unguium shorter period than that of the marketed oral preparation due to good permeability, good retention capacity and conservation of high activity in nail plate as well as the potent antifungal activity thereof based on the present invention. Another object of the present invention is to provide the effective therapeutic agent for onychomycosis exhibiting no side effect even if therapeutically effective amounts of it are administered sufficiently.

More concretely, the present invention provides a therapeutic agent for onychomycosis containing a compound having a formula (1):

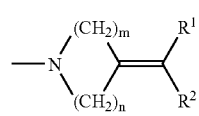

(I)

Wherein $R^1$ and $R^2$ are the same or different and are hydrogen atom, $C_{1-6}$ alkyl group, a non-substituted aryl group, an aryl group substituted with 1 to 3 substituents selected from a halogen atom, trifluoromethyl group, nitro group and $C_{1-6}$ alkyl group, $C_{2-8}$ alkenyl group, $C_{2-6}$ alkinyl group, or $C_{7-12}$ aralkyl group, m is 2 or 3, n is 1 or 2, or a salt thereof as active ingredient.

In addition, "presence" includes the mean of "remaining".

BRIEF DESCRIPTION OF DRAWINGS

FIG. 4 is a graph showing a distribution of the number of fungal cells in the skin of a guinea pig model of tinea pedis in each treated group according to the evaluation method of the drug effect in the present invention.

BEST MODE FOR CARRYING OUT THE INVENTION

Figure 1A:
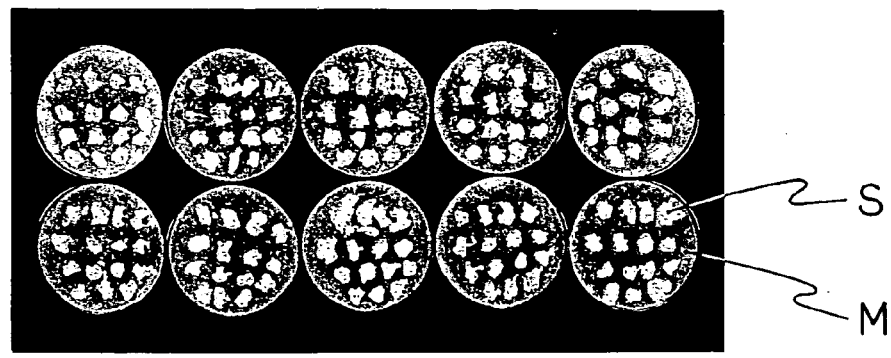
FIG. 1 is a color copy of a photograph to identify the agent remaining in the skin which is previously evaluated by the conventional method in the detecting method of the antimicrobial agent five days after last treatment in the present invention. The note (a) shows the infected control group, (b) the KP-103-treated group, (c) the lanoconazole-treated group.

As an animal employed in the present invention, there includes mammal such as mice, rat, guinea pig or rabbit. As a biosample, there includes a skin of back or planta, a nail or the like, which is taken from such animal.

A method for infecting such animal or biosample with a pathogenic microorganism includes an inoculation percutaneously, orally, intravenously, transbronchially, transnasally or intraperitoneally. Especially in case of the skin, there includes a method for inoculating it on the skin, a method for inoculating on the exposed demis, the closed patch method, intracutaneous injection or the like. Incase of the nail, there includes a method for inoculating on nail, a method in which a skin of the animals' foot is infected by the above-mentioned infecting method to the skin, and thereafter the infection is moved into the nail by leaving it for several months.

The term "skin" means a tissue including the three layers being epidermis, demis and subcutaneous tissue, accompanied by pilus (hair), nail, glandulae sebaceae, glandulae sudoriferae and glandulae mammaria as appendages. The epidermmis is separated five layers being stratum corneum, stratum lucidum, granulosum epidermidis, stratum spinosum, and stratum basale from surface in order. The stratum corneum, the stratum lucidum and the stratum granulosum epidermidis is referred to as a stratum corneum in a broad sense. Herein, keratin substance means a part of the above-mentioned stratum corneum.

The term "nail" includes nail plate, nail bed, nail matrix, further side nail wall, posterial nail wall, eponychium and hyponychium which make up a tissue around thereof.

In the present invention, the term "pathogenic microorganism" means a microorganism which causes human and animal disease in one way or another. An example of the pathogenic microorganism (hereinafter referred to "microorganism") is bacteria including aerobic Gram-negative *bacillus* and coccus such as *Pseudomonas* and Neisseriaceae species; facultative anaerobic Gram-negative *bacillus* such as *Eschrichia, Salmonella* and *Enterobacter* species; Gram-positive coccus such as *Staphylococcus* and *Streptococcus* species. The other examples of microorganism are fungi including Hyphomycetes such as *Trichophyton, Microsporum* and *Epidermophyton* species; Blastomycetes such as *Candida* and *Malassezia*; Ascomycetes such as *Aspergillus* species; Zygomycetes such as *Mucor* species; and variants thereof. Examples of such variants are resistant strain which naturally obtains drug resistance; auxotrophic mutation strain which comes to have nutritious dependency; artificial mutation strain which is artificially mutated by treatment with mutagenic agent; and the like.

Mycosis means a disease which is caused by invading and proliferating in the tissue of human or animal. Usually, mycosis is broadly divided into superficial mycosis and deep mycosis. A seat of the disease lie in the skin or visible mucosa in case of the former, in viscus, central nervous system, subcutaneous tissue, muscle, born or articulation in case of the latter. Chief example of superficial mycosis is dermatophytosis which is caused by infecting with dermatophyte such as *Trichophyton, Microsporum* and *Epidermophyton* species, including three disease, tinea, tinea favosa and tinea imbricata. Tinea may be conventionally employed a synonymous with dermatophytosis. In addition, dermatophyte belonging to *Trichophyton* species is referred usually to as trichophytosis.

In the present invention, an antimicrobial agent means a compound having an antimicrobial effect or a composition containing the compound. The composition includes a preparation form being artificial composition and a natural composition such as a natural product.

A method for administration of the antimicrobial agent in the present invention depends on the kind thereof and includes topical application, subcutaneous administration, oral administration, intravenous administration or the like.

When the method for detecting the pathogenic microorganism, the method for evaluating the drug effect and the method for detecting the antimicrobial agent according to the present invention is carried out, either an infection with microorganism or an administration of the antimicrobial agent may be carried out first. Especially, in the method for evaluating the drug effect of the present invention (hereinafter referred to "the present evaluation method"), a therapeutic effect of the antimicrobial agent can be evaluated in case where the antimicrobial agent is administered after the infection with microorganism, meanwhile, a effect of the antimicrobial agent protecting from the infection and the retention capacity thereof can be evaluated in case where the infection with microorganism is carried out after the administration of the antimicrobial agent. In order to evaluating the retention capacity of the antimicrobial agent, the evaluation can be carried out with varying the period until infection with microorganism from the administration of the antimicrobial agent.

In the present invention, it is preferable to use dialysis or ultra filtration for removing the antimicrobial agent in view point of the usefulness, but not limited thereto as long as a microorganism to be a detecting target or a microorganism used in the present evaluation method and the like is not affected by it.

In dialysis, a marketed dialysis membrane made of cellulose is convenient. A membrane made of the other material can be used without problem, as long as the microorganism to be the detecting target or the microorganism used in the present evaluation method and the like can not be passed, and the antimicrobial agent can be passed through it. Since sizes of most fungi and bacteria are at least 0.2 μm, it is preferable to use the membrane having less than 0.2 μm of the pore size, particularly it is suitable to use dialysis membrane having fractional molecular weight of 1,000 to 50,000.

As out side solutions used in dialysis, there include physiological saline, distilled water, phosphate buffered physiological saline, the other buffer and the like.

In removing the antimicrobial agent according to the present invention, even though the infected site with the microorganism is the nail, organ or the like as well as the skin, the antimicrobial agent can be efficiently removed. Usually, since there is the case where it takes longer time dialysis to remove the antimicrobial agent from nail than skin, the following treatment with digestive enzyme may be carried out before removing it in order to enhance the removal effect.

Dialysis conditions depend on variety, dose concentration, dose term and the drug holidays (the term until evaluation from last day of treatment) of an antimicrobial agent. Therefore, it is preferable to previously investigate the dialysis conditions enabling the antimicrobial agent to be removed from the treated skin about individual cases using the following detecting method of the existing antimicrobial agent in the infected site with a microorganism in the present invention (hereinafter referred to "the present method for detecting an agent") to adjust the conditions appropriately.

Whether an antimicrobial agent has been removed can be easily determined using the following method.

The present method for detecting an agent is carried out by placing and cultivating the infected site with a microorganism which is subjected to the removing method of the antimicrobial agent (e.g. an skin piece) or a suspension obtained according to the following extraction procedure of the microorganism from the above skin piece on an agar medium containing the microorganism, and observing a growth inhibition of the microorganism found around it. When there is the remaining antimicrobial agent, the growth inhibition of the microorganism is observed.

The present evaluation method can be carried out by locating and cultivating, on a medium, the skin piece in which a removal of an antimicrobial agent has been determined using the above-mentioned present method for detecting the agent after carrying out the appropriate removal of the antimicrobial agent and observing whether there is a growth of microorganism or not, or by smearing and cultivating a suspension obtained according to the extraction procedure of the microorganism from the skin piece on an agar medium and observing whether there is the growth of microorganism or not or counting colonies emerging on those medium.

A treatment with trypsin can be carried out in order to extract a microorganism efficiently from a biosample such as a skin or a nail. Other digestive enzyme than trypsin such as pronase or keratinase, or a keratin resolvent such as urea also can be used without limitation to trypsin as long as they have an extraction effect. It is necessary to adjust concentrations of the digestive enzyme such as trypsin and keratin resolvent in a treating solution, and reaction time to no affect range to a microorganism. The treatment with digestive enzyme such as trypsin may be carried out either before or after dialysis.

When the treatment with trypsin is carried out before dialysis, it is necessary to remove the digestive enzyme sufficiently so that the microorganism is not affected on dialysis.

As a medium used for a cultivation of a microorganism in the present invention, any medium can be used as long as it can be conventionally used for the cultivation and a separation of the microorganism. In case of fungi, example of the medium is Sabouraud medium, modified Sabouraud medium, Czapek agar medium, Potato dextrose agar medium or the like. On the other hand, in case of bacteria, example of the medium is Mueller Hinton medium, modified Mueller Hinton medium, Heart Infusion agar medium, Brain Heart Infusion agar medium, normal agar medium or the like.

A reacting temperature is 10 to 40° C., preferably 20 to 40° C. A microorganism may be cultivated with standing during a sufficient time when the microorganism can be growth, for example, 1 to 20 days in case of fungi, 1 to 5 days in bacteria.

The present evaluation method be utilizable as a evaluation method of a drug effect in exo vivo which comprises infecting a skin, a nail excised from an animal body with a microorganism, thereafter administering an antimicrobial agent as a test compound, then removing the antimicrobial agent and detecting and determining quantity of the microorganism in the sample.

The present evaluation method also can be applied to an evaluation of an antimicrobial agent such as a therapeutic agent for deep mycosis or an antibacterial agent as well as an evaluation of an effect of a therapeutic agent for superficial mycosis. That is to say, it is possible to evaluate an effect of a therapeutic agent for deep mycosis or an antibacterial agent by means of administering an antimicrobial agent to an animal infected with a microorganism such as a fungus or a bacterium by inoculating percutaneously, orally, intravenously, transbronchially, transnasally, intraperitoneally, then obtaining biosample such as skin, kidney, lung or brain, and detecting the viable microorganism in the biosample in which removed the remaining antimicrobial agent has been removed.

In addition, the present evaluation method enables a quantitative comparison of antimicrobial effects by means of determining the number of viable microorganisms in the treated biosample.

That is to say, a significant deference test is carried out about the number of microorganisms in the infected site with the microorganism for the treated group with drug and for the reference infected group using a statistical method such as Kruskal-Wallis Test, and thereby a quantitative comparison between the groups can be done by using a multiple test such as Tukey method.

The present invention is useful as either a method for evaluating a drug effect or a method for detecting the antimicotics in keratin substance or nail, after administering the antifungus to the patient infected with fungus. For example, according to the present invention, an effect of an antifungal agent can be evaluated by administering it to the patient whose skin or nail is infected with fungus, obtaining the keratin substance or nail, then removing the above-mentioned antifungal agent, and thereafter detecting the viable fungus in the keratin substance or nail. Additionally, according to the present invention, a detection of an antifungal agent can be carried out by administering it to the patient whose skin or nail is infected with fungus, then obtaining the keratin substance or nail, cultivating it on agar medium containing fungus, and thereafter detecting the existing antifungal agent in the keratin substance or nail through a growth inhibition of fungus observed around the keratin substance or nail. Such evaluation of an antifungal agent administered to a patient with fungus and detection of the antifungal agent from the keratin substance or nail can be carried out in the same manner as in the above-mentioned evaluation method of a drug effect and detecting method of the antimicrobial agent administered to an animal or a biosample.

Furthermore, the present invention provides various useful antimicrobial agents according to the present evaluation method. As the antimicrobial agent obtained by the present evaluation method, there is an antimicrobial agent comprising a compound having an eradication effect for microorganism in vivo or a composition for therapy of the superficial mycosis, deep mycosis or bacterial infection containing the compound; an antimicrobial agent having the true effect selected by means of showing a statistically significant effect; furthermore, an antimicrobial agent having an excellent eradication effect for microorganism in vivo, which is selected by means of appearing the pure antimicrobial activity thereof; or an antimicrobial agent of the complete cure type without relapse. A concrete example is a therapeutic agent for onychomycosis comprising a compound having the group represented by the above-mentioned formula (I). Among them, more preferable concrete example is a therapeutic agent for onychomycosis comprising the compound represented by the formula (II):

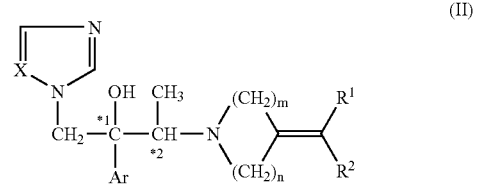

(II)

wherein, Ar is a non-substituted phenyl group or a phenyl group substituted with 1 to 3 substituents selected from a halogen atom and trifluoromethyl group, $R^1$ and $R^2$ are the same or different and are hydrogen atom, $C_{1-6}$ alkyl group, a non-substituted aryl group, an aryl group substituted with 1 to 3 substituents selected from a halogen atom, trifluoromethyl group, nitro group and $C_{1-6}$ all group, $C_{2-8}$ alkenyl group, $C_{2-6}$ alkinyl group, or $C_{7-12}$ aralkyl group, m is 2 or 3, n is 1 or 2, X is nitrogen atom or CH, and

*1 and *2 mean an asymmetric carbon atom.

In the above-mentioned formula (I) or (II), the substituted phenyl group is a phenyl group having 1 to 3 substituents selected from a halogen atom and trifluoromethyl, and includes, for instance, 2,4-difluorophenyl, 2,4-dichlorophenyl, 4-fluorophenyl, 4-chlorophenyl, 2-chlorophenyl, 4-trifluoromethylphenyl, 2-chloro-4-fluorophenyl, 4-bromophenyl or the like. $C_{1-6}$ alkyl group includes, for example, a straight chain, branched chain or cyclic alkyl group having 1 to 6 carbon atoms such as methyl, ethyl, n-propyl, isopropyl, n-butyl, isobutyl, sec-butyl, tert-butyl, n-pentyl, isopentyl, neopentyl, tert-pentyl and cyclohexyl. The non-substituted aryl group includes, for example, phenyl, naphthyl, biphenyl or the like. The substituted aryl group includes, for example, 2,4-difluorophenyl, 2,4-dichlorophenyl, 4-fluorophenyl, 4-chlorophenyl, 2-chlorophenyl, 4-trifluoromethylphenyl, 2-chloro-4-fluorophenyl, 4-bromophenyl, 4-tert-butylphenyl, 4-nitrophenyl or the like. $C_{2-8}$ alkenyl group includes, for example, vinyl, 1-propenyl, styryl or the like. $C_{2-6}$ alkynyl group includes, for example, ethynyl or the like. $C_{7-12}$ aralkyl group includes, for example, benzyl, naphthylmethyl, 4-nitrobenzyl or the like.

In addition, the most preferable compound among the above-mentioned antimicrobial agent includes the compound which shows the therapeutic efficiency like the following KP-103.

The above-mentioned KP-103 means an antifungal indicated by (2R,3R)-2-(2,4-difluorophenyl)-3-(4-methylenepiperidine-1-yl)-1-(1H-1,2,4-triazole-1-yl)butane-2-ol. The compound can be prepared by allowing (2R,3S)-2-(2,4-difluorophenyl)-3-methyl-2-[(1H-1,2,4-triazole-1-yl)methyl]oxirane to react with 4-methylenepiperidine based on Example 1 in WO94/26734.

An effectiveness of the KP-103 used as an antifungal in the present invention for onychomycosis has not been confirmed, but its antifungal activity has been already known (WO94/26734).

The antimicrobial agent obtained in such manner can be used as a drug composition, the drug composition in order to sterilize a microorganism. In other words, it comes to be a drug composition which cures disease such as mycosis completely, and prevents a relapse.

Onychomycosis means a kind of the above-mentioned superficial mycosis, in the other word a disease which is caused by invading and proliferating in the nail of human or an animal. *Trichophyton rubrum* and *Trichophyton mentagrophytes* mainly cause onychomycosis in human. In rare case, *Microsporum, Epidermophyton, Candida, Aspergillus* or *Fusarium* causes it.

As a disease which is susceptible to treat with a therapeutic agents for onychomycosis of the present invention, there is included tinea unguium caused by *Trichophyton* species, Onychocandidasis caused by *Candida* species or onychomycosis (sensu stricto) caused by the other fungus.

When a therapeutic agent for onychomycosis being a kind of antimicrobial agent in the present invention is given as topical preparation, there is liquid preparation, cream, ointment or manicure preparation as dosage form. In this case, it can be prepared using oil vehicle, emulsion vehicle or the like. The preferable amount of active ingredient is in 0.1 to 10% by weight. A dose amount may be appropriately aligned depending on the width of affected area and condition of disease.

In case of an oral preparation, it is used as powder, tablet, granule, capsule or syrup. In addition, it is used in form of injection such as subcutaneous injection, intramuscular injection or intravenous injection.

In the present invention, although the dosage amount of a therapeutic agent for onychomycosis depends on age, weight and individual conditions of a patient, it is about 10 mg to about 10 g per day, preferably about 50 mg to about 5 g as amount of the active ingredient. The agent was given in the above-mentioned daily dose at once or several divided portions.

The present invention is further explained in details based on the Examples hereinafter, but is not limited thereto.

PRETREATMENT OF COMPARATIVE EXAMPLE 1 AND EXAMPLES 1 TO 3

[1] Preparation of Fungal Solution and Production of a Guinea Pig Model of Interdigital Type of Tinea Pedis.

Millipore Filter (made by Millipore Corporation, HA, diameter 47 mm, 0.45 μm) was placed on Brain-Heart-infusion agar medium (available from Nissui Pharmaceutical Co., LTD.), and $10^6$ cells of microcondium of *Trichophyton mentagrophytes* KD-04 strain were applied thereon. The cultivation was carried out at 30° C. under 17% of $CO_2$ for 7 days. After the cultivation, just amount of physiological saline containing 0.05% of Tween 80 was dropped on the filter and arthroconidia were collected using a platinum loop. After a hyphal mass was removed by a filtration with a sterile gauze, the number of arthroconidia in the filtrate was calculated by hemocytometer to adjust in concentration of $1 \times 10^8$ arthroconidia/ml to obtain a fungal inocula.

A guinea pig model of interdigital type of tinea pedis was prepared according to the method of Arika et al (Antimicrobial Agents and Chemotherapy, 36: 2523–2525, 1992). Concretely, in two hind foots of male Hartley strain guinea pigs of 7 weeks age, the interdigital skin was lightly abraded with sandpaper. A paper disc (AAdisc available from Whatmen International Ltd cut in 8×4 mm) moisten with the above-mentioned solution of the inoculated organism was applied onto the region between the interdigital toes of the hind feet and fixed using Self-adhering-Foam Pad (Restone 1560M; available from 3M) and adhesive stretch bandage (ELASTPORE; available from Nichiban Co., Ltd). The paper disc and the bandage were removed seven days after of the infection.

[2] Preparation of Drug-Solution and Topical Treatment for the Guinea Pig Model of Interdigital Type of Tinea Pedis A marketed 1% lanoconazole solution (commercial name: Astat (trade name) solution) and a solution in which KP-103 was solved in a concentration of 1% in polyethylene grycole #400: ethanol (75:25 v/v) mixture were used as test substance. Each solution in amount of 0.1 ml was applied to the plantar skin once a day from 10 days after the infection for 10 days.

COMPARATIVE EXAMPLE 1

Conventional Method for Evaluating Drug Effect

The conventional method was described as follows. For the infected control group without an application of the drug, the KP-103-treated group and the lanoconazole-treated group, 10 guinea pigs (hereinafter referred to "animal") were employed, respectively. Animals of each group were sacrificed two days after and 30 days after the last treatment. Their two hind feet were excised and wiped with the cotton sweb containing alcohol sufficiently. A skin of whole sole was excised and cut into 15 skin pieces in total including 12 skin pieces from plantar parts and 3 skin pieces from an interdigital part. Each skin pieces were placed on 20 ml of Sabouraud dextrose agar medium (available from Difco laboratories) containing 50 μg of chloramphenicol (available from Wako Pure Chemical Industries, Ltd.), 100 μg of gentamicin (available from Schering-Plough Corporation), 50 μg of 5-fluorocytosine (available from Wako Pure Chemical Industries, Ltd.) and 1 mg of cycloheximide (available from nacalai tesque, Inc.) per ml. An antibiotic substance added to the medium was set to a condition which enable bacteria not to grow and which enable fungi to grow without problem. After 10 days cultivation at 30° C., the result is described as "fungus-negative" when no growth of fungus was observed in all skin pieces, and the number of fungus-negative feet was determined. In the evaluation of the effect 30 days after last treatment, two days after the last treatment the treated feet were wiped with a cotton swab containing alcohol and fixed with the bandage in order to prevent a reinfection. The bandage was changed once a week. The therapeutic effects of KP-103 and lanoconazole two days after and 30 days after the last treatment are shown in Table 1.

TABLE 1

| Test substance | The number of fungus-negative feet/ Total number of infected feet | |
|---|---|---|
| | Two days after the last treatment | 30 days after the last treatment |
| Infected control | 0/20 | 0/20 |
| KP-103 | 20/20 | 16/20 |
| Lanoconazole | 20/20 | 9/20 |

As shown in the Table 1, in the KP-103-treated group, fungus-negative was observed in all feet two days after the last treatment, and also fungus-negative was observed in 16 out of 20 feet 30 days after the last treatment. On the other hand, in the lanoconazole-treated group, fungus-negative was observed in all feet two days after the last treatment, but fungus-negative was observed in only 9 feet 30 days after the last treatment, and there is no correlation between the therapeutic effects two days after and 30 days after the last treatment. The number of fungus-negative feet decreased 30 days after the last treatment. It was thought that the therapeutic effect of lanoconazole observed two days after the last treatment resulted from the inhibition of the growth of fungus caused by an interfusion of the drug remaining in the treated skin into culture system, because lanoconazple had a potent in vitro antifungal activity against dermatophytes, it was eight-fold more active than KP-103 against *Trichophyton* with a growth inhibitory concentration of 15.6 ng/ml. The determination test of the remaining agent was carried out.

EXAMPLE 1

Determination of drug remaining in skin which has been already evaluated five days after the last treatment according to conventional method.

A model was prepared according to Comparative Example 1. Lanoconazole being a test compound was used for a therapeutic experience as 1% solution with the same vehicle as KP-103. For the infected control group without an application of a drug, the KP-103-treated group and the lanoconazole-treated group, 20 animals were employed, respectively. The two hind feet were excised from each animal five days after the last treatment in the same manner as in Comparative Example 1. A total of 20 light feet were used for an evaluation by the conventional method, and a total of 20 right feet were used in the present evaluation method.

Figure 1B:
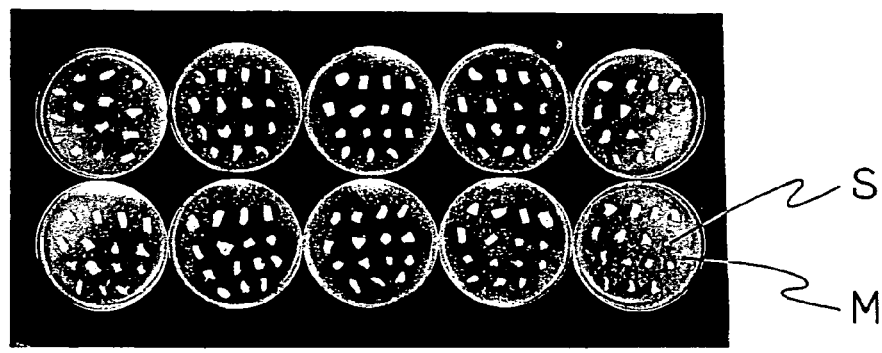
Figure 1C:
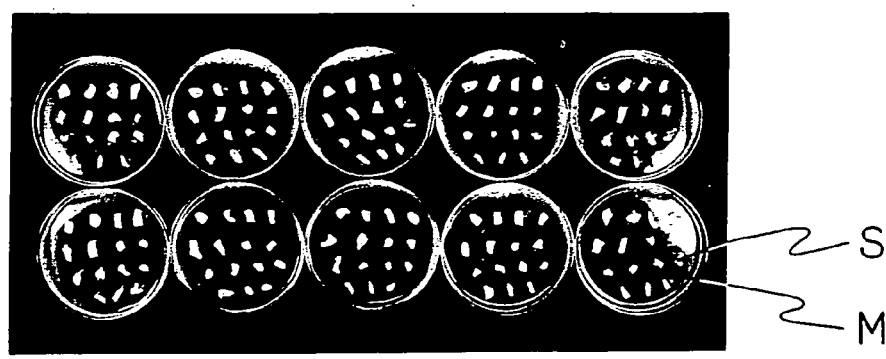

The skin pieces of light foot were placed on 20 ml of Sabouraud dextrose agar medium containing *Trichophyton mentagrophytes* KD-04 strain ($2\times10^4$ cells/ml) and the antibiotic substance described in Comparative Example 1. After the cultivation was carried out at 30° C. for 3 days, a growth inhibitory-zone of fungus appeared around the skin was observed and was photographed for 10 out of 20 feet. FIG. 1 is an electronic date of the photograph of the skin after the cultivation in the above-mentioned condition. (a) indicates the infected control group without the drug application, (b) the KP-103-treated group and (c) the lanoconazole-treated group. One plate was explained as a representative of ten plates corresponding to each animal in the infected control group (a). In FIG. 1, S indicates one of 15 skin pieces of planta derived from the animal and M the above-mentioned medium. S and M described in both the KP-103-treated group (b) and the lanoconazole-treated group (c) are also the same. In the medium, the white zone shows the growth of fungus, on the other hand, the black zone shows the inhibition of the growth of fungus.

As shown FIG. 1, a good growth of the fungus was observed around the skin piece of the infected control group without any drug. In the group treated with KP-103, the growth of fungus was observed in all skin pieces, although in around the skin pieces the growth of fungus was slightly inhibited as compared with the infected control group. On the other hand, the growth of fungus was completely inhibited in around the skin pieces treated with lanoconazole. As these results, the therapeutic effect of lanoconazole in the conventional method shown in Table 1 was considered as an apparent therapeutic effect such that the agent remaining in the skin come to be mixed in culture system to inhibit the growth of fungus.

Therefore, it came to appear that the drug effect could not be evaluated by the conventional method precisely.

EXAMPLE 2

Determination of Remaining Drug after Removing Drug from Skin.

As Example 1, 20 right feet were excised from each animal five days after the last treatment, and sufficiently wiped with the cotton sweb containing alcohol. The planta was cut off from each foot. The skin mincced by a scissors was put into dialysis membrane (fractional molecular weight: 12,000–14,000, made of cellulose, available from VISKASE SALES Corporation) together with 4 ml of distilled water. Dialysis was carried out under 3 L of distilled water at 4° C. for 2 days. The dialysis water was changed twice a day 4 times in total. The content was transfer into a glass homogenizer. Thereto 4 ml double-concentration phosphate buffered saline containing 4% of trypsin derived from pig pancreas (available from BIOZYME Laboratories Limited) was added and the resulting mixture was homogenized. It was left at 37° C. for one hour and was filtrated with the two-ply gauze. The resulting filtrate was centrifuged. To a precipitate obtained by removing the supernatant were added 8 ml of phosphate buffered saline containing 2% of trypsin and further it allow to react with shaking at 37° C. for one hour. After a centrifugation, the precipitate obtained by removing the supernatant was washed three times by centrifuging with phosphate buffered saline in order to remove trypsin. To the precipitate 2 ml of the same saline were added to prepare a suspension thereof.

Figure 2A:
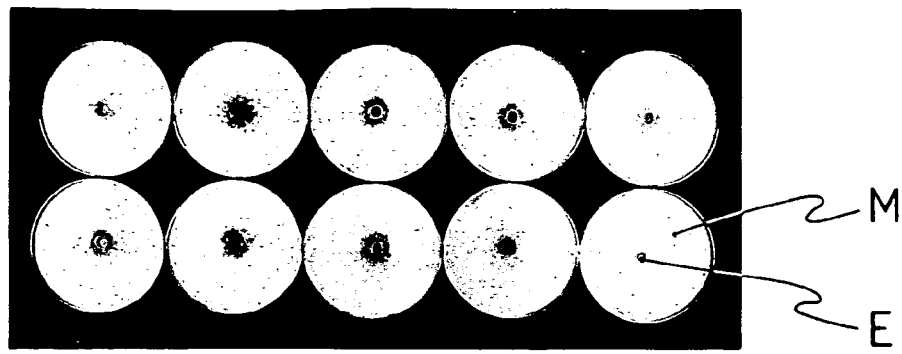
FIG. 2 is a color copy of photograph to identify agent remaining in the skin which is previously evaluated by the detecting method of the antimicrobial agent five days after last treatment in the present invention. The note (a) shows the infected control group, (b) the KP-103-treated group, (c) the lanoconazole-treated group.
Figure 2B:
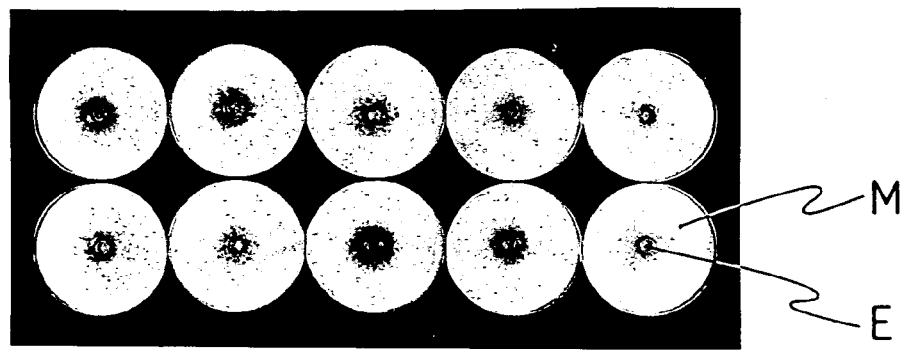
Figure 2C:
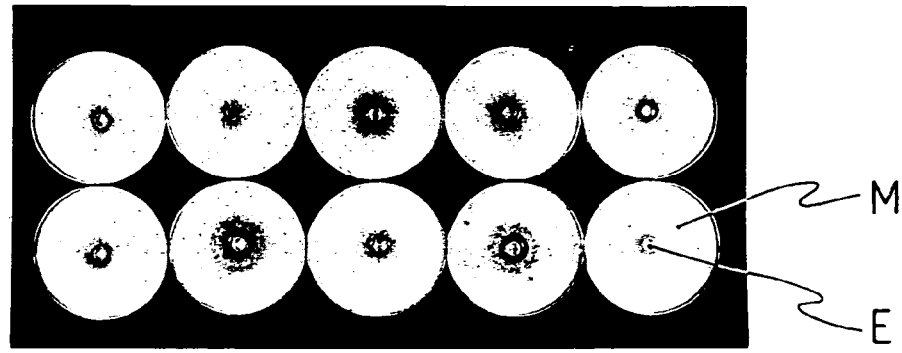

When dialysis and the treatment with trypsin were carried out using the same fungus used in this Example, an affect of these procedures on a survival rate of fungus could not be observed. Previously, a well was prepared in the center of Sabouraud dextrose agar medium (20 ml) containing *Trichophyton mentagrophytes* KD-04 strain ($2\times10^4$ cells/ml) and the antibiotic substance described in Comparative Example 1. Into the well 100 μl of the above-mentioned suspension were added to cultivate at 30° C. for three days. After the cultivation, a growth inhibitory-circle of fungus appeared was observed and was photographed for 10 out of 20 feet. FIG. 2 is an electronic date of the photograph of the skin after the cultivation in the above-mentioned condition. (a) indicates the infected control group without the drug application, (b) the KP-103-treated group and (c) the lanoconazole-treated group. One plate was explained as a representative often plates corresponding to each animal in the infected control group (a). In FIG. 2, E indicates the skin suspension prepared from planta of the animal and M the above-mentioned medium. E and M described in both the KP-103-treated group (b) and the lanoconazole-treated group (c) are also the same. In the whole medium, the white zone shows the growth of fungus, on the other hand, the black zone around the well shows the inhibition of the growth of fungus.

In FIG. 1 showing the conventional method, no growth of fungus was observed in around the skin of the lanoconazole-treated group taken five days after the last treatment and the remaining drug was determined in the skin. By contrast, in FIG. 2, although few growth-inhibitory circle was observed in 2 out 10 feet suspension obtained by removing the drug using dialysis treatment of the present invention for the skin of the lanoconazole-treated group taken five days after the last treatment, the growth-inhibitory circle was never observed in residual 8 feet.

Since it came to appear that the drug remaining in treated skin could be sufficiently removed using dialysis according to the present invention, it was confirmed that the evaluation of the drug effect was not affect by the remaining drug.

EXAMPLE 3

Detection of Viable Fungus in Skin and Evaluation of Drug Effect

To two mediums of Sabouraud dextrose agar medium (20 ml) containing the antibiotic substance described in Comparative Example 1 were applied 100 µl of the suspension from one right feet of each animals obtained in Example 2. After the cultivation was carried out at 30° C. for 10 days, the result is described as "fungus-negative" when a colony of fungus was not observed in two agar plates (detection limit: 10 CFU (colony forming unit)/feet). The number of fungus-negative feet was counted. On the other hand, 20 left feet were evaluated in the same manner as in Comparative Example 1. Table 2 shows the result of comparing the therapeutic effect evaluated by the conventional method with that by the present evaluation method.

TABLE 2

|  | The number of fungus-negative feet/Total number of infected feet | |
| --- | --- | --- |
| Test substance | Conventional Method | Present evaluation method |
| Infected control | 0/20 | 0/20 |
| KP-103 | 19/20 | 17/20 |
| Lanoconazole | 20/20 | 3/20 |

In case of the group treated with KP-103, no significant difference was observed in the number of fungus-negative feet, even if the number was evaluated by either the conventional method or the present evaluation method, as shown in Table 2. The rate of a fungus-negative foot evaluated by the present evaluation method is 85% in case of KP-103. On the other hand, in the group treated with lanoconazole, although "fungus-negative" was observed in all feet by the conventional method, but "fungus-negative" was just observed in only three feet by the present evaluation method.

As mentioned above, it came to appear that using the present evaluation method, a true drug effect can be substantially evaluated without an affect by the remaining drug after the treatment therewith.

Furthermore, a result in the present evaluation method correlates with a result obtained by evaluation in the conventional method described in Comparative Example 1 in 30 days after the last treatment. Thereby, by using the present evaluation method, an effect of an antimicrobial agent to prevent a relapse can be estimated by the evaluation at early time after a treatment. Therefore, a complete cure type of the antimicrobial agent without the relapse can be obtained by using the present evaluation method.

PRETREATMENT OF EXAMPLES 4 AND 5

[1] Preparation of Fungal Solution and Production of Guinea Pig Model of Tinea Unguium and Tinea Pedis.

A fungal solution was prepared in the same manner as in the pretreatment of Comparative Example 1 except for changing *Trichophyton mentagrophytes* KD-04 strain to *Trichophyton mentagrophytes* SM-110 strain.

A guinea pig model of tinea unguium and tinea pedis was prepared in the same manner as in the above-mentioned preparation of the guinea pig model in interdigital tinea pedis except for changing male Hartley strain guinea pigs of 7 weeks age to male Hartley strain guinea pigs of 5 weeks age and except that the paper disc and the bandage was removed 21 days after the infection changing from seven days after the infection. The invasion of dermatophytes in plantar skin and nail plate was observed 60 days after the infection.

[2] Preparation of Drug Solution and Treatment of Guinea Pig of Tinea Unguium and Tinea Pedis As test compounds, solutions were prepared by dissolving raw powders of KP-103, amorolfine and terbinafine in a concentration of 1% thereof to mixture solution of polyethylene grycole #400: ethanol (75:25 v/v), respectively. Capsule of terbinafine was prepared by crushing the marketed tablet, suspending in the concentration of 100 mg/ml into Miglyol 812 (available from Mitsuba trade Co., Ltd)with glass homogenizer uniformity, and injecting the resulting suspension into each capsule in the concentration of 40 mg/kg depending on body weight measured on administration day. A solution of KP-103, amorolfine or terbinafine in the amount of 0.1 ml was applied a plantar skin and nail of one foot once a day for 30 consecutive days. In case of terbinafine capsule, one capsule (40 mg/kg) was administered orally.

EXAMPLE 4

Evaluation of Drug Effect on Tinea Unguium

The effect on tinea unguium was evaluated by the following method.

Figure 3:
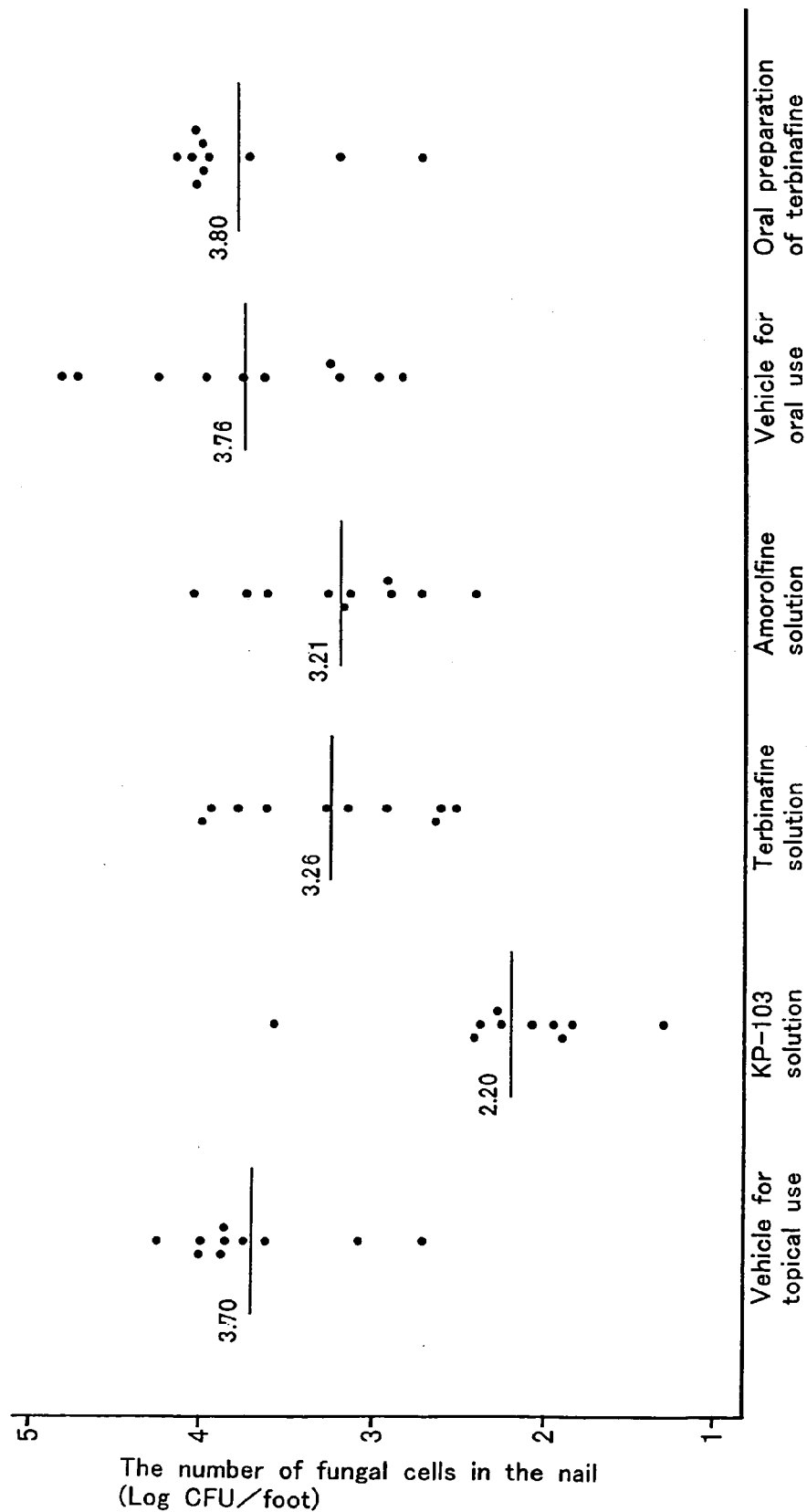
FIG. 3 is a graph showing a distribution of the number of fungal cells in the nail of a guinea pig model of tinea unguium in each treated group according to the evaluation method of the drug effect in the present invention.

Animals were sacrificed two days after the last treatment. One hind foot was excised and wiped sufficiently with the cotton sweb containing alcohol. Nails (three in total) of one hind foot was excised and miced by a scissors. It was transferred into glass homogenizer and was homogenized adding 4 ml double-concentration phosphate buffered saline (Phosphate Buffered Salts, available from Takara Shuzo Co., Ltd.) containing 4% of trypsin derived from pig pancreas (available from BIOZYME Laboratories Limited). The reaction was carried out with shaking at 37° C. for one hour. After a centrifugation, the obtaining precipitate was washed three times by centrifuging with phosphate buffered saline in order to remove trypsin. The precipitate was suspended with 4 ml of distilled water and put into dialysis membrane (fractional molecular weight: 12,000–14,000, made of cellulose, available from VISKASE SALES Corporation). Dialysis was carried out into 3 L of distilled water at 4° C. for 14 days. Dialysis water was replaced twice a day 28 times in total. After a centrifugation, 1 ml of phosphate buffered saline was added to the precipitate obtained by removing the supernatant to prepare a suspension. This suspension was defined as stock solution and was diluted by tenfold. To Sabouraud dextrose agar medium (20 ml) containing the antibiotic substance described in Comparative Example 1 were added 100 μl of the stock solution or the dilution. After the cultivation was carried out for 10 days, the result was described as "fungus-negative" when no colony of fungus was observed in all medium (detection limit: 10 CFU/feet). The number of fungus-negative feet in the nail was counted. When the colony was appeared on the medium, the number of colonies (CFU) was counted to calculate the number of colonies in the nail of one foot by the dilution rate. After Kruskal Wallis Test was carried out for the number of fungi in the nail, the multiple comparison was carried out based on Tukey method to analysis the significant difference between groups. Those results were shown in FIG. 3 and Table 3 thereof was made. In FIG. 3, the number of CFU in nails in each treated group was plotted and the mean number of CFU was shown by horizontal line and numerical value.

Using the above-mentioned suspension, sufficient removal of the remaining drug was determined by the present evaluation method in the same manner as in Example 2.

EXAMPLE 5

Evaluation of Drug Effect on Tinea Pedis

Skin pieces of hind feet were excised from each animal described in Example 4. A removal of the drug and a determination of the remaining drug were carried out in the same as in Example 2 except that dialysis for removing the drug carried out for 3 days and that dialysis water was changed six times in total. The sufficient removal of the remaining drug was confirmed.

Then the drug effect was evaluated in the same manner as in Example 4 (detection limit: 20 CFU/feet). Those results were shown in FIG. 4 and Table 4 thereof was made. In FIG. 4, the number of CFU in the skin in each treated group was plotted and the mean number of CFU was shown by horizontal line and numerical value.

TABLE 3

| Test substance | The number of feet with fungus-negative nail/ Total number of infected feet | Mean number of fungal cells in the nail (Log CFU ± SD) |
|---|---|---|
| Vehicle for topical use | 0/10 | 3.70 ± 0.44 |
| KP-103 solution | 0/10 | 2.20 ± 0.56** |
| Amorolfine solution | 0/10 | 3.26 ± 0.54 |
| Terbinafine solution | 0/10 | 3.21 ± 0.47 |
| Vehicle for oral use | 0/10 | 3.76 ± 0.67 |
| Oral preparation of terbinafine | 0/10 | 3.80 ± 0.44 |

**significant difference versus the vehicle for topical use, the vehicle for oral use and the oral preparation of terbinafine in 0.01% of significant level is shown.

As shown in FIG. 3 and Table 3, no foot with fungus-negative nail was observed in all groups treated with substance tested for 30 days. But, KP-103 significantly reduced the number of fungal cells in the nail as compared with the vehicle for topical use. The therapeutic effect thereof was significantly superior to the oral preparation of terbinafine. On the other hand, no significant fungicidal effect was seen in amorolfine and terbinafine (for external use, oral use) as compared with the vehicle. The therapeutic effect thereof was not seen. As mentioned above, it was suggested that KP-103 exhibited the therapeutic effect on tinea unguium by topical application and that KP-103 could cure tinea unguium earlier than the oral preparation of terbinafine.

TABLE 4

| Test substance | The number of feet with fungus-negative skin/ Total number of infected feet | Mean number of fungal cells in the skin (Log CFU ± SD) |
|---|---|---|
| Vehicle for topical use | 0/10 | 4.37 ± 0.33 |
| KP-103 solution | 10/10** | <1.3** |
| Amorolfine solution | 4/10 | 1.74 ± 0.45* |
| Terbinafine solution | 10/10** | <1.3** |
| Vehicle for oral use | 0/10 | 3.85 ± 0.68 |
| Oral preparation of terbinafine | 10/10** | <1.3** |

*significant difference versus the vehicle for topical use in 0.05% of significant level is shown.
**significant difference versus the vehicle for topical use and the vehicle for oral use in 0.01% of significant level is shown.

As shown in FIG. 4 and Table 4, the excellent therapeutic effect on tinea pedis was seen in all drugs, KP-103, terbinafine and amorolfine in either case where it was evaluated by the rate of fungus-negative foot or where by the number of fungal cells in the skin. On the other hand, it became clear that KP-103 exhibited the excellent fungicidal effect on tinea unguium, although terbinafine and amorolfine did not exhibited the therapeutic effect on tinea unguium as shown in FIG. 3 and Table 3.

INDUSTRIAL APPLICABILITY

As mentioned above, recently developed drugs having an extremely potent activity against *Trichophyton* in vitro such as lanoconazole brings about the judgement of fungus-negative according to the conventional method regardless of the existence of the no-treated fungus in the skin, since the drug remaining in the treated skin inhibits a growth of the fungus in the skin.

On the contrary, according to the present invention, an effect of an antimicrobial agent can be evaluated accurately, since a remaining drug can be removed by dialyzing the infected site with a microorganism of animal or biosample such as the treated skin using a dialysis membrane. Furthermore, although it is difficult to quantitatively compare of an antimicrobial effect such as an antifungal effect in conventional method, the present evaluation method enables the antimicrobial effects to compare quantitatively, since the number of viable fungi in the infected site of an animal or a bioample such as a skin can be determined precisely. In addition, the therapeutic effect based on the present evaluation method reflect a result as to relapse in the conventional method and therefore an effect to prevent relapse can be estimated by evaluating at earlier time after the treatment according to the present evaluation method. Therefore, in the present evaluation method, a true effect of an antimicrobial agent can be evaluated and it is possible to select an antimicrobial agent having an excellent sterilization effect against fungi in vivo or an antimicrobial agent of complete cure type which does not bring about relapse. As mentioned above, the present evaluation method is very useful as a method for evaluating the antimicrobial agent.

Additionally, in onychomycosis it is the first time that it is possible to evaluate a therapeutic effect against onychomycosis on a model of tinea unguium by the present evaluation method.

As a result of the evaluation of the therapeutic effect against onychomycosis according to the present evaluation method, it comes to clear that KP-103 exhibits the excellent therapeutic effect against onychomycosis with a simple application on which the effect is not exhibited using the conventional topical antifungal agent. Therefore, KP-103 is a beneficial agent for treating onychomycosis, industrially.

The invention claimed is:

1. A method for treating a subject having onychomycosis wherein the method comprises topically administering to a nail of said subject having onychomycosis a therapeutically effective amount of an antifungal compound represented by the following formula:

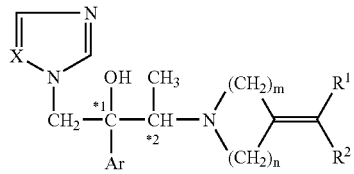

(II)

wherein, Ar is a non-substituted phenyl group or a phenyl group substituted with 1 to 3 substituents selected from a halogen atom and trifluoromethyl group, $R^1$ and $R^2$ are the same or different and are hydrogen atom, $C_{1-6}$ alkyl group, a non-substituted aryl group, an aryl group substituted with 1 to 3 substituents selected from a halogen atom, trifluoromethyl group, nitro group and $C_{1-16}$ alkyl group, $C_{2-8}$ alkenyl group, $C_{2-6}$ alkynyl group, or $C_{7-12}$ aralkyl group, m is 2 or 3, n is 1 or 2, X is nitrogen atom or CH, and

*1 and *2 mean an asymmetric carbon atom.

2. The method of claim 1, in which the compound represented by the formula (II) is (2R, 3R)-2-(2,4-difluorophenyl)-3-(4-methylen piperidine-1-yl)-1-(1H-1,2,4-triazole-1-yl)butane-2-ol.

* * * * *

UNITED STATES PATENT AND TRADEMARK OFFICE

(12)  CERTIFICATE EXTENDING PATENT TERM
UNDER 35 U.S.C. § 156

| | | | |
|---|---|---|---|
| (68) | PATENT NO. | : | 7,214,506 |
| (45) | ISSUED | : | May 8, 2007 |
| (75) | INVENTOR | : | Yoshiyuki Tatsumi et al. |
| (73) | PATENT OWNER | : | Kaken Pharmaceutical Co., Ltd. |
| (95) | PRODUCT | : | JUBLIA® (efinaconazole) |

This is to certify that an application under 35 U.S.C. § 156 has been filed in the United States Patent and Trademark Office, requesting extension of the term of U.S. Patent No. 7,214,506 based upon the regulatory review of the product JUBLIA® (efinaconazole) by the Food and Drug Administration. According to United States Patent and Trademark Office records, the original expiration date of the patent as of the date of issuance of this certificate is October 5, 2021. Because it appears that the requirements of the law have been met, this certificate extends the term of the patent for the period of

(94)                                            1,601 days subject to the payment of maintenance fees as provided by law, with all rights pertaining thereto as provided by 35 U.S.C. § 156.

I have caused the seal of the United States Patent and Trademark Office to be affixed this 1st day of February 2021.

Drew Hirshfeld
Performing the Functions and Duties of the
Under Secretary of Commerce for Intellectual Property and
  Director of the United States Patent and Trademark Office